United States Patent [19]

Keunecke et al.

[11] 4,269,776

[45] May 26, 1981

[54] JET PUMP EXHAUST RECYCLE IN PRODUCTION OF PHTHALIC ANHYDRIDE

[75] Inventors: Gerhard Keunecke, Geyen; Herbert Krimphove, Pulheim, both of Fed. Rep. of Germany

[73] Assignee: Davy Powergas GmbH, Cologne, Fed. Rep. of Germany

[21] Appl. No.: 117,143

[22] Filed: Jan. 30, 1980

Related U.S. Application Data

[63] Continuation-in-part of Ser. No. 49,836, Jun. 18, 1979, abandoned, and a continuation-in-part of Ser. No. 110,571, Jan. 9, 1980, abandoned.

[30] Foreign Application Priority Data

Jun. 16, 1978 [DE] Fed. Rep. of Germany ....... 2826346

[51] Int. Cl.$^3$ .......................................... C07D 307/89
[52] U.S. Cl. ............................... 260/346.4; 260/346.7
[58] Field of Search .......................... 260/346.4, 346.7

[56] References Cited

U.S. PATENT DOCUMENTS

| 3,528,997 | 9/1970 | Juston et al. | 260/346.7 X |
| 3,655,521 | 4/1972 | Gehrken et al. | 260/346.7 X |

*Primary Examiner*—Richard Raymond
*Attorney, Agent, or Firm*—Millen & White

[57] ABSTRACT

In a process for the production of phthalic anhydride comprising a stage of catalytic oxidation of a mixture of o-xylene or naphthalene and air, a stage of separation of the crude phthalic anhydride from the reaction gas by cooling, and a stage of purification of the crude phthalic anhydride by rectification under vacuum, said vacuum being maintained by at least one jet pump, the improvement which comprises employing compressed air as the operating medium for said jet pump, and recycling resultant compressed air loaded with the exhaust gas to a process gas upstream of the phthalic anhydride separation stage, said process gas being any gas leading to the separation stage, preferably the gas between the oxidation stage and the separation stage.

10 Claims, 3 Drawing Figures

JET PUMP EXHAUST RECYCLE IN PRODUCTION OF PHTHALIC ANHYDRIDE

CROSS REFERENCE TO RELATED APPLICATIONS

This is a continuation-in-part of abandoned application Ser. No. 049,836 filed June 18, 1979, and continuation application, Ser. No. 110,571, filed Jan. 9, 1980, now abandoned.

BACKGROUND OF THE INVENTION

This invention relates to a process for the production of phthalic anhydride by catalytic oxidation of a mixture of o-xylene or naphthalene and air, separation of the crude phthalic anhydride from the reaction gas by cooling, and purification of the crude phthalic anhydride by thermal pretreatment and rectification under vacuum, wherein the vacuum is maintained by jet pumps.

In the distillative purification of crude phthalic anhydride, it is conventional to employ rectification under pressures of, for example, 20–300 mm. Hg, preferably 40–100 mm. Hg. Heretofore, the vacuum was generally produced by two-stage steam ejector installations or water ring pumps. In the vacuum line leading from the column to the vacuum pump, a sublimator or a sublimate trap is generally disposed, wherein the vapors taken in by the vacuum line are cooled to 50°–70° C. and partially condensed. Despite this precaution, volatile distillation products pass through the vacuum line into the steam ejector or water ring pump where they are dissolved by the cooling water of the steam ejectors and/or by the operating water of the water ring pump. The thus-contaminated water must be purged periodically or continuously, resulting in a wastewater entailing considerable treatment expense. Moreover, the sublimator must be cleaned from time to time to ensure troublefree operation, i.e., the deposits formed therein must be dissolved with a solvent or melted off; furthermore, due to fumaric acid formation in the deposit, difficulties are frequently encountered in this step. Finally, the steam ejectors must be heated to avoid precipitation of the evacuated, organic vapors in the ejector which would otherwise foul the ensuing pumping operation.

SUMMARY OF THE INVENTION

An object of the present invention, therefore, is to eliminate the aforesaid wastewater problem; and another object is to simplify the vacuum operation by dispensing with the sublimator in the vacuum line.

Upon further study of the specification and appended claims, further objects and advantages of this invention will become apparent to those skilled in the art.

To attain these objects, there is provided a process wherein compressed air, instead of steam, is employed as the operating medium for the jet pumps, and the resultant contaminated compressed air utilized for evacuation is combined with any process stream upstream of the phthalic anhydride separation step. In this way, it is possible for the entire amount of the vapors and gases evacuated from the distillation column into the vacuum line to be taken in by the air jet pump. An intermediate separation in a cooled sublimator is no longer necessary. The operating air thus loaded with the evacuated gases and vapors, passes with the process gas stream into the phthalic anhydride separation stage. Residual gas from the separation step is then passed into a conventional waste gas purification stage, for example, into a waste gas scrubbing stage, which is required even in prior art processes.

By the present process, the phthalic anhydride vapors evacuated into the vacuum line are separated in the separators whereas any taken-in vapors of maleic anhydride and other compounds such as the monocarboxylic acids are ultimately removed from the waste gas in the scrubbing stage. In contrast thereto, if the wastewaters obtained during the vacuum operation with steam ejectors or water ring pumps were to be concomitantly employed in the waste gas scrubbing stage, a considerably larger energy consumption would be involved for the required concentration of the increased scrubbing solution volume for purposes of combustion, as well as for maleic anhydride production. In addition, the phthalic anhydride taken into the vacuum line would pass, insofar as it was not trapped in the sublimator, into the scrubbing solution and would thus constitute losses for phthalic anhydride manufacture. Furthermore, it would be difficult to process the scrubbing solution to obtain pure maleic anhydride.

Preferably, the compressed air is preheated before use for evacuation to temperatures of between 30° and 200° C., preferably between 100° and 200° C., and more preferably between 130° and 150° C. In this way, the evacuated vapors are not condensed in the air jet pump and in the subsequent conduits which would otherwise lead to disturbances in the pumping operation. Furthermore, the provision is made that an operating air pressure is employed ranging between 2 and 20 bar, preferably between 4 and 10 bar.

In accordance with the preferred embodiment of the process of this invention, the gases are evacuated from the distillation stages without intermediate cooling. The capital outlay for the sublimator as well as its operating costs (supplied with cooling oil and heating oil) are thus eliminated. Also, upsets in operation due to fumaric acid formation in the sublimator are no longer encountered.

Preferably, gases and vapors from storage tanks containing phthalic anhydride are likewise evacuated by air jet pumps, and the air loaded with these gases and vapors is also recycled into the process gas stream. In this way, phthalic anhydride vapors from phthalic anhydride tanks, especially liquid phase storage tanks, are not passed into the atmosphere, thereby avoiding both product loss and environmental pollution. These tanks are suitably ventilated by a heated gas, for example, nitrogen, to avoid condensation of phthalic anhydride in the suction line. The air jet pumps under these circumstances generally pull a vacuum of 1 to 5 mm. Hg absolute pressure.

The air pressure at the downstream sides of the pumps is generally in the range from 500 to 1000 mm water-column above atmospheric pressure. The air passing the pumps is decreased in pressure to this level.

Preferably, the vapor-laden air used in the air jet pumps is combined with the process gas stream between the catalytic oxidation stage and the phthalic anhydride separating stage. Evacuated phthalic anhydride is thus recovered in the separators, whereas maleic anhydride and other volatile compounds, such as monocarboxylic acids, are removed in the waste gas purifying stage, for example, by being scrubbed out from the waste gas.

The catalytic oxidation step is conventional and is generally conducted at 340°–390° C. and the reaction gas is conventionally cooled to about 45°–65° C. during the separating step.

DETAILED DESCRIPTION OF THE DRAWING

Figure 1:
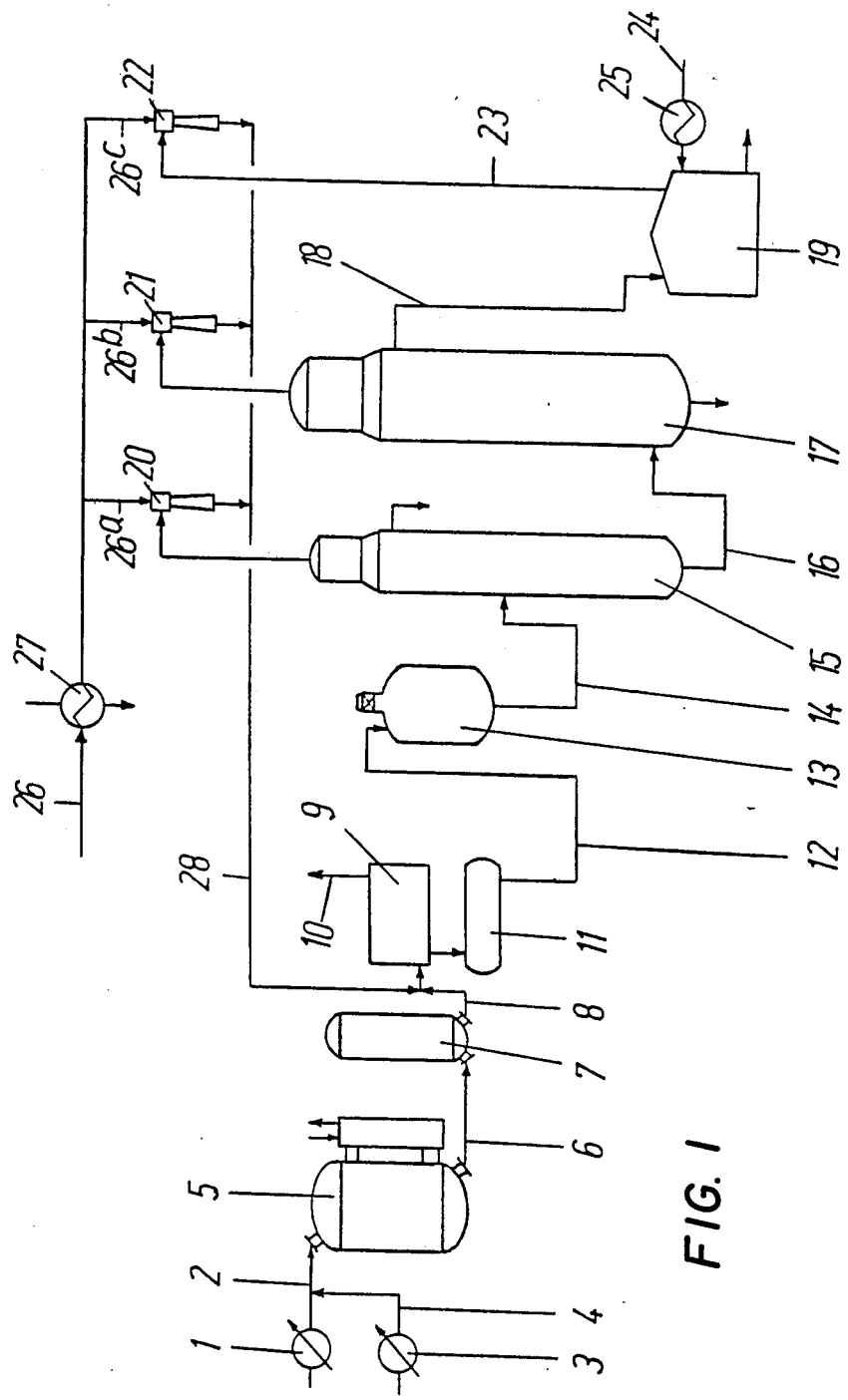
FIG. 1 is a schematic flow chart of a preferred system for conducting the process of this invention.

Referring to FIG. 1, it is seen that the air fed via conduit 2 is heated in the air preheater 1 and then mixed with o-xylene fed via conduit 4, which o-xylene has been preheated in heater 3. The o-xylene/air mixture is catalytically oxidized in reactor 5 with the formation of phthalic anhydride. The process gas leaves the reactor 5 at 380° C., passes through conduit 6 into the gas cooler 7 wherein it is cooled to 170° C., and then into the separator 9 via conduit 8. In the separator, the gaseous stream is cooled to about 55° C. and the phthalic anhydride is separated in the solid phase. The waste gas, essentially free of phthalic anhydride exits from separator 9 at 10 and is fed to a scrubbing stage (not shown) wherein maleic anhydride, monocarboxylic acids, and other volatile components are scrubbed out before the waste gas is passed out into the environment.

Periodically, the phthalic anhydride deposited in separator 9 is removed by melting and collected in the crude PA container 11. The crude phthalic anhydride is conducted from container 11 via conduit 12 to the pretreatment tank 13. Under practical conditions, several such pretreatment stirrer tanks are connected in series; for the sake of simplicity, however, only one of these is illustrated. The pretreated, crude phthalic anhydride passes via conduit 14 into the preliminary rectification column 15 where a forerun is separated under a vacuum of 250 mm. Hg. The crude product, thus liberated of readily volatile impurities, passes via conduit 16 into the primary rectification column 17 wherein the pure phthalic anhydride is distilled overhead under a vacuum of 150 mm. Hg, while the residue is withdrawn from the sump. The pure product is conducted via conduit 18 into the pure product collecting tank 19 wherein it is stored in the liquid phase and from there it is fed to a conventional flaker (not shown.)

Columns 15 and 17 are connected via vacuum lines to the air jet pumps 20 and 21, respectively, which maintain the columns under the aforementioned vacuum. To simplify the illustration, respectively only one air jet pump has been indicated; under practical conditions, respectively two air jet pumps can be connected in series. In a similar way, anhydride vapors are exhausted from the collecting tank 19 by means of an air jet pump 22 via conduit 23. During this step, nitrogen is fed to the gas space of tank 19 via conduit 24, this nitrogen being preheated in heat exchanger 25.

The air jet pumps 20, 21, 22 are operated with compressed air of 6 atmospheres absolute, which air is fed via conduit 26 to a heat exchanger 27, heated with condensing vapor and then via the branch conduits 26$^a$, 26$^b$, and 26$^c$ to the air jet pumps 20, 21, 22. The air from the air jet pumps laden with the vapors exhausted from columns 15, 17 and tank 19 is collected in conduit 28, the latter being connected to the process gas line 8 leading from the gas cooler 7 to the separator 9, so that the laden air is conducted through the separator 9 combined with the process gas.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE

In a plant as shown in principle in the figure, 7.5 tons/hour of o-xylene are oxidized with 170,000 Nm$^3$/h. of air in a contact oxidation with the usual V$_2$O$_5$ catalyst, thus producing phthalic anhydride. The stream of reaction gas is cooled to 55° C. In this way, 7.7 tons/hour of crude phthalic anhydride is obtained with a PA content of 99.5%.

The crude phthalic anhydride is then purified in a conventional way by thermal pretreatment and two-stage distillation in columns under a head pressure of 250 mm. Hg and 150 mm. Hg, respectively. The pure product is stored in a collecting tank.

To produce the vacuum for the distillation columns and to evacuate vapors from the storage tank, air jet pumps are employed which operate with air preheated to 150° C. under 6 atmospheres absolute. The air consumption is 500 Nm$^3$/h. The air laden with the exhaust vapors is combined with the process gas stream upstream of the separators. The waste gas from the separators is fed to a scrubbing stage for purification, wherein 2 m$^3$/h. of scrubbing solution is obtained with 30% by weight of organic compounds.

COMPARATIVE EXAMPLE

The procedure of the above example is followed, but using two-stage steam ejectors in place of air jet pumps. For condensation purposes, 5 tons/hour of steam and cooling water are required. At the steam ejectors, 5 m$^3$/h. of waste-water is produced which is utilized during the scrubbing of the waste gases leaving the separator. In this way, 3.6 m$^3$/h. of scrubbing solution is obtained having 20% by weight of organic compounds.

The preceding examples can be repeated with similar success by substituting the generically or specifically described reactants and/or operating conditions of this invention for those used in the preceding examples.

Figure 2:
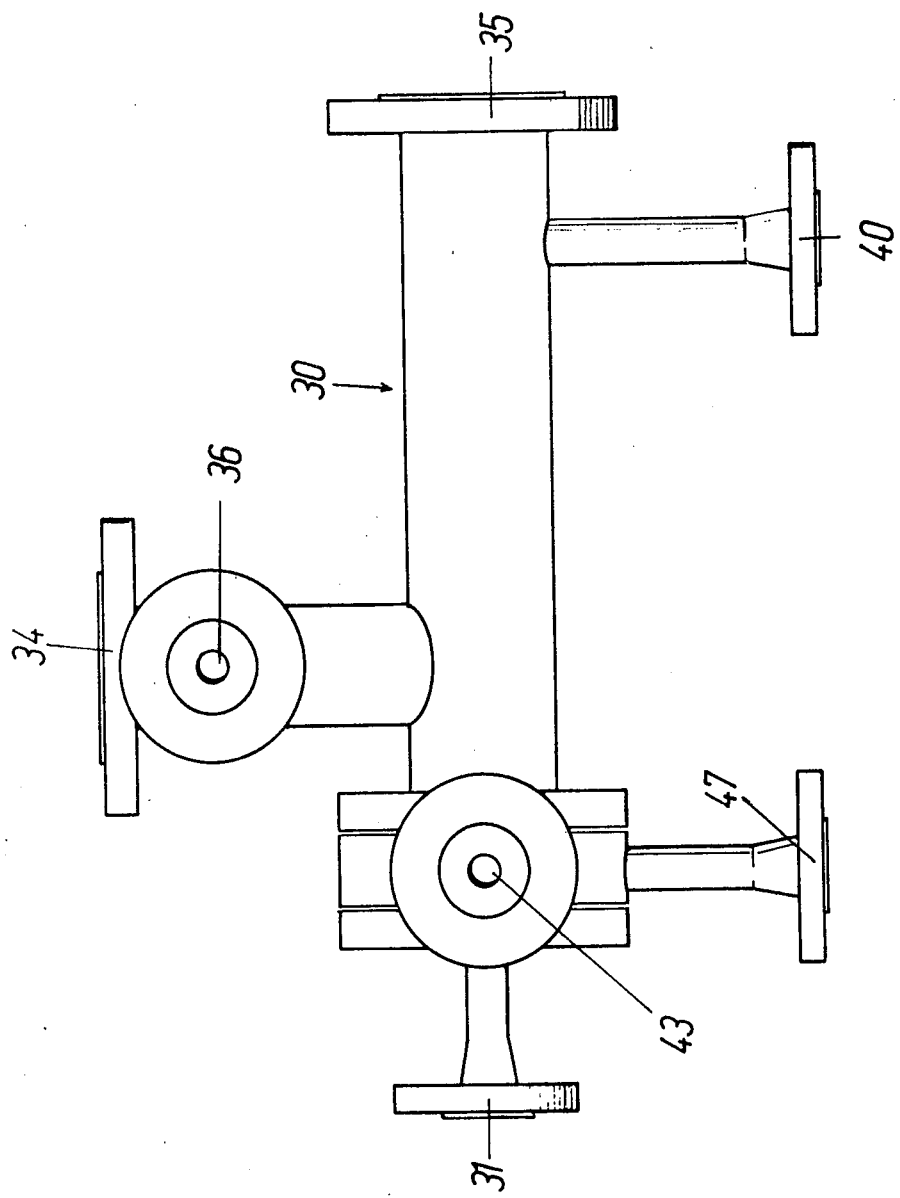
FIG. 2 is a side elevation of an air jet pump of this invention.
Figure 3:
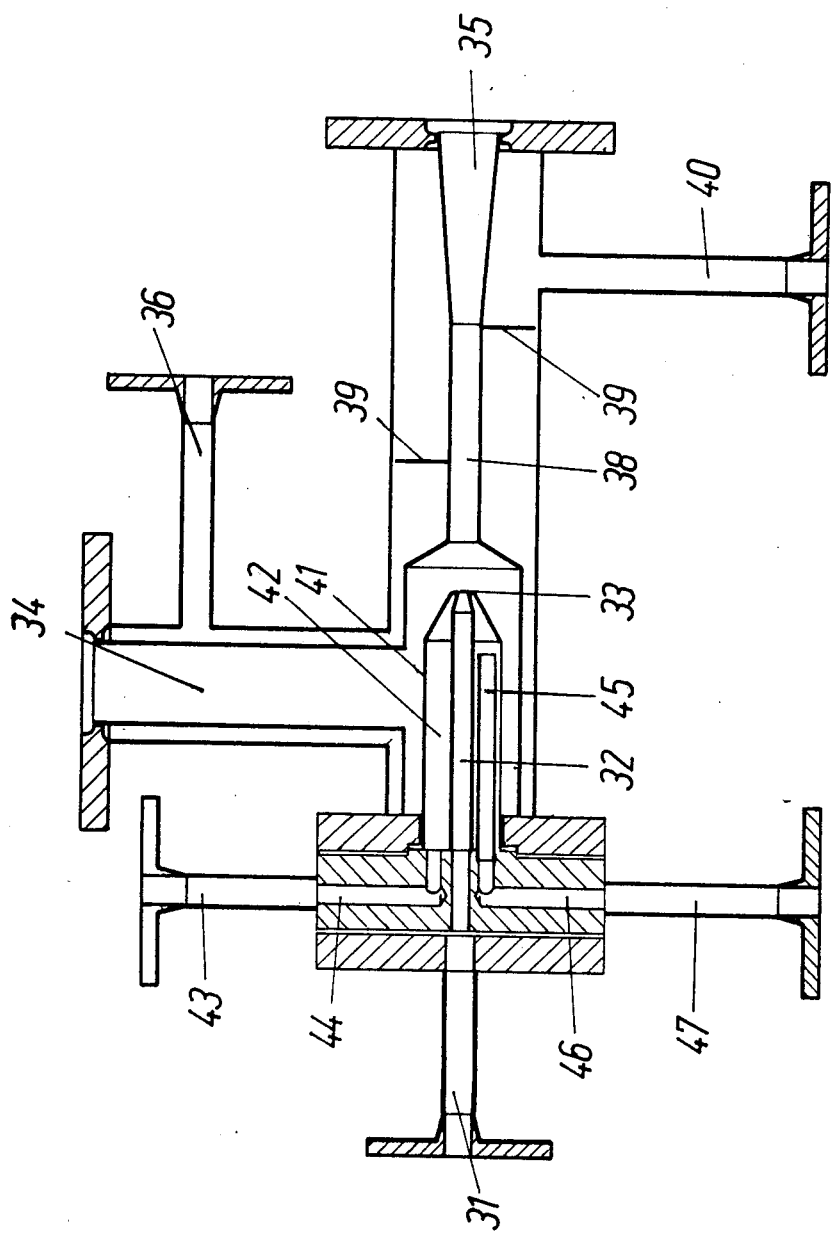
FIG. 3 is a longitudinal section thereof.

Referring now to FIGS. 2 and 3, the air jet pump is designated as 30. The driving air enters the pump from line 26 through flange tube 31 with e.g. 6 bar. It is accelerated on its passage via channel 32 and exits as a jet of high velocity through nozzle 33. The distillation columns and, if desired, the storage tank(s) to be exhausted are connected to the flange tube 34. A suction-and-carryover effect is provided in the neighborhood of the air jet emitted through nozzle 33 so that gases and vapors are sucked through flange tube 34 into the air jet. The vapor/air mixture is discharged through the flanged diffusor tube 35 into line 28. To avoid the condensation of the vapors in the pump 30 all the walls contacted by the sucked-in vapors are heated by condensing steam. A first part of the steam is fed with 6 bar and 164° C. through flange tube 36 and passes aroung tube 34, the chamber 37 and the tubes 38 and 35. The baffles 39 assure a good contact of the tubes 38, 35 by the condensing steam. The condensate is withdrawn through flange tube 40. The inner tube 41 comprises a heating jacket 42 in order to avoid the condensation on the tube. The second part of the steam is fed through flange tube 43 and bores 44 and condenses in the jacket 42. The condensate is collected in the tube 45 at the bottom of the jacket and is drawn off through bores 46 and flange tube 47.

If two of these air jet pumps are connected in series the flange tube 35 of the first pump is connected to the flange tube 34 of the second pump, and the flange tube 35 of the second pump is connected to line 28.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. In a process for the production of phthalic anhydride comprising a stage of catalytic oxidation of a mixture of o-xylene or naphthalene and air, a stage of separation of the crude phthalic anhydride from the reaction gas by cooling, and a stage of purification of the crude phthalic anhydride by rectification under vacuum, said vacuum being maintained by at least one jet pump, the improvement which comprises employing compressed air as the operating medium for said jet pump, and recycling resultant compressed air loaded with the exhaust gas to a process gas upstream of the phthalic anhydride separation stage, said process gas being any gas leading to the separation stage.

2. A process according to claim 1, wherein the compressed air is preheated, prior to being passed through the jet pump, to 30°–200° C.

3. A process according to claim 1, wherein the compressed air is preheated, prior to being passed through the jet pump, to 100°–200° C.

4. A process according to claim 1, wherein the pressure of the compressed air is between 2 and 20 bar.

5. A process according to claim 3, wherein the pressure of the compressed air is between 4 and 10 bar.

6. A process according to claim 1, said exhaust gas being withdrawn from the rectification stage without intermediate cooling.

7. A process according to claim 1, wherein purified phthalic anhydride is stored in the liquid phase in a storage container, and a jet pump operated by compressed air is employed to maintain a vacuum on said storage container, and recycling resultant compressed gas loaded with exhaust gas into a process gas upstream of the phthalic anhydride separation stage.

8. A process according to claim 1, wherein the resultant compressed air loaded with exhaust gas is combined with a process gas stream between the oxidation stage and the phthalic anhydride separating stage.

9. A process according to claim 6, wherein the resultant compressed air loaded with exhaust gas is combined with a process gas stream between the oxidation stage and the phthalic anhydride separating stage.

10. A process according to claim 7, wherein the resultant compressed air loaded with exhaust gas is combined with a process gas stream between the oxidation stage and the phthalic anhydride separating stage.

* * * * *

UNITED STATES PATENT AND TRADEMARK OFFICE
CERTIFICATE OF CORRECTION

PATENT NO. : 4,269,776
DATED : May 26, 1981
INVENTOR(S) : Gerhard Keunecke et al.

It is certified that error appears in the above—identified patent and that said Letters Patent is hereby corrected as shown below:

ON THE TITLE PAGE:

Assignee: reads "Davy Powergas, GmbH, Cologne, Fed. Rep. of Germany"

should read -- Davy McKee Aktiengesellschaft, Federal Republic of Germany --.

Signed and Sealed this

Sixteenth Day of March 1982

|SEAL|

Attest:

GERALD J. MOSSINGHOFF

Attesting Officer  Commissioner of Patents and Trademarks